(12) United States Patent
Rodoper

(10) Patent No.: US 8,830,174 B1
(45) Date of Patent: Sep. 9, 2014

(54) VARIABLE PROFILE INPUT BUTTON

(75) Inventor: Mete Rodoper, Sunnyvale, CA (US)

(73) Assignee: Amazon Technologies, Inc., Reno, NV (US)

( * ) Notice: Subject to any disclaimer, the term of this patent is extended or adjusted under 35 U.S.C. 154(b) by 287 days.

(21) Appl. No.: 13/247,800

(22) Filed: Sep. 28, 2011

(51) Int. Cl.
  *G06F 3/02* (2006.01)

(52) U.S. Cl.
  USPC ......... 345/168; 345/156; 345/169; 340/407.2

(58) Field of Classification Search
  CPC ..... G06F 3/02; G06F 3/0202; H01H 13/7066; H01H 13/81
  USPC .......... 345/156, 168, 169, 173, 184; 310/311, 310/339; 340/407.1, 407.2; 708/142; 200/512
  See application file for complete search history.

(56) References Cited

U.S. PATENT DOCUMENTS

| | | | |
|---|---|---|---|
| 6,555,774 B1 * | 4/2003 | Nielsen | 200/343 |
| 8,309,870 B2 * | 11/2012 | Peterson et al. | 200/344 |
| 2002/0054060 A1 * | 5/2002 | Schena | 345/701 |
| 2002/0130673 A1 * | 9/2002 | Pelrine et al. | 324/727 |
| 2004/0164971 A1 * | 8/2004 | Hayward et al. | 345/179 |
| 2005/0157893 A1 * | 7/2005 | Pelrine et al. | 381/190 |
| 2006/0238079 A1 * | 10/2006 | Pei et al. | 310/339 |
| 2007/0152974 A1 * | 7/2007 | Kim et al. | 345/168 |
| 2009/0002205 A1 * | 1/2009 | Klinghult et al. | 341/33 |
| 2009/0007758 A1 * | 1/2009 | Schlosser et al. | 84/436 |
| 2009/0189873 A1 * | 7/2009 | Peterson et al. | 345/173 |
| 2009/0211336 A1 * | 8/2009 | Combes et al. | 73/23.37 |
| 2011/0111852 A1 * | 5/2011 | Cohen et al. | 463/37 |
| 2012/0105333 A1 * | 5/2012 | Maschmeyer et al. | 345/173 |
| 2012/0126959 A1 * | 5/2012 | Zarrabi et al. | 340/407.1 |
| 2012/0206248 A1 * | 8/2012 | Biggs | 340/407.2 |
| 2012/0242592 A1 * | 9/2012 | Rothkopf et al. | 345/173 |
| 2012/0268384 A1 * | 10/2012 | Peterson et al. | 345/170 |
| 2012/0302323 A1 * | 11/2012 | Gagner et al. | 463/25 |
| 2012/0319956 A1 * | 12/2012 | Talach et al. | 345/168 |

* cited by examiner

*Primary Examiner* — Joe H Cheng
(74) *Attorney, Agent, or Firm* — Lee & Hayes, PLLC

(57) ABSTRACT

One or more buttons on an electronic device are mechanically coupled to actuators utilizing electroactive polymers. When active, the electroactive polymer deploys the button such that a height of the button above a substrate is increased. When inactive, the button returns to a stowed position having a lower height, and thus presents a lesser profile.

22 Claims, 7 Drawing Sheets

VARIABLE PROFILE INPUT BUTTON

BACKGROUND

Electronic devices that accept input from users are ubiquitous, and include cellular phones, electronic book (eBook) readers, tablet computers, desktop computers, portable media devices, and so forth. This input may be accepted using buttons or keys which the user touches. However, traditional buttons consume significant volume within devices, particularly when not in use.

BRIEF DESCRIPTION OF THE DRAWINGS

The detailed description is set forth with reference to the accompanying figures. In the figures, the left-most digit(s) of a reference number identifies the figure in which the reference number first appears. The use of the same reference numbers in different figures indicate similar or identical items.

DETAILED DESCRIPTION

Overview

Electronic devices may use buttons or keys to accept user input. These buttons may be arranged into keypads or keyboards, allowing the device to receive input from users such as characters, commands, and so forth. Portable electronic devices such as tablet computers and smartphones continue to become more compact. In these more compact forms, the volume available for buttons and their associated mechanisms continues to be reduced. As these available volumes decrease, the overall experience in using those buttons may suffer. For example, low profile buttons may have minimal key travel, resulting in unsatisfying user feedback.

Described herein are devices and techniques for variable profile buttons. These variable profile buttons are configured to transition from a stowed position having a first profile (or height) to a deployed position having a second profile. In some implementations, the button may be configured to attain one or more intermediate profiles.

When stowed, the variable profile buttons are configured such that an upper outer shell of the button, which the user may touch during use, is at a first height. This height may be adjusted such that the upper outer shell is coplanar with a surface of the device. As a result, the device presents a flat, low profile surface when stowed. When deployed, the variable profile buttons extend above this first height. By increasing this height, a vertical distance which the button travels when actuated increases. This vertical distance is also known as "key travel." Increasing key travel, as well as force response provided to the user provides improved haptic feedback to the user. This improved haptic feedback, such as the tactile experience of actually "pushing" the button may also improve usability and user satisfaction.

As described herein, the variable profile buttons may use one or more solid-state actuators to generate the displacement of the buttons. As used herein, a solid-state actuator is a material or materials which readily transitions between at least two physical states, each having different physical dimensions. For example, the transition may include shortening or lengthening. The solid-state actuator may be activated to change physical states upon application of electric, magnetic, chemical, or other external input. Solid-state actuators include electroactive polymers, dielectric electroactive polymers, ionic polymer-metal composites, piezoelectric ceramics, and so forth.

Changes in characteristics of the solid-state actuator may be used to determine when the button is pressed. This allows the solid-state actuator to operate as an actuator and a sensor. For example, a change in the capacitance of a dielectric electroactive polymer may be detected and used to signal a button press. In other implementations, a separate detector may be used. For example, a membrane switch may be configured such that when the button is depressed, an electrical circuit is established.

Illustrative Device

Figure 1:
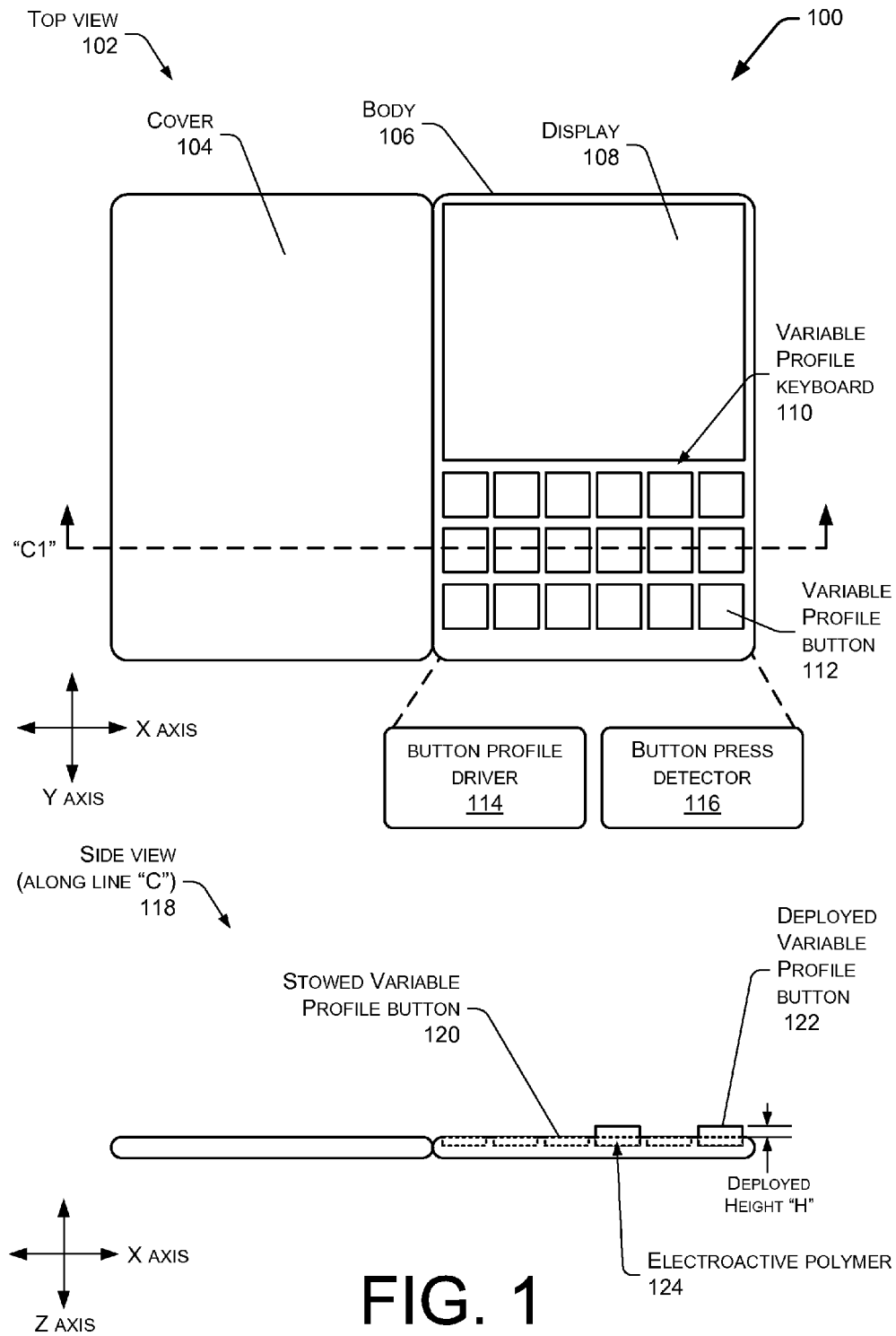
FIG. 1 depicts an electronic device configured with a variable profile keyboard.

FIG. 1 depicts an electronic device 100 configured with a variable profile keyboard. A top view 102 shows a cover 104 coupled to a body 106. This coupling may comprise a hinge or other joint. The cover 104 is configured to articulate such that it covers a front of the body 106 when in a closed state. In some implementations, the cover 104 may be omitted.

Also shown is a display 108 configured to present information to the user. In some implementations, the display 108 may be combined with a touch sensor to provide a touch-sensitive display, or touchscreen display.

Within or coupled to the device is a variable profile keyboard 110 comprising variable profile buttons 112. These variable profile buttons 112 are configured to vary between at least two states. These two states are a stowed position in which the button is at a first height and a deployed position in which the button is at a second height greater than the first height.

A button profile driver 114 is configured to provide power or other inputs to the variable profile buttons 112 to initiate a change between the stowed and deployed positions. To generate these inputs, the button profile driver 114 may comprise an electrostatic generator, buck/boost circuitry configured to deliver a pre-determined voltage and amperage to the button, microfluidic chemical distribution system, photon source, and so forth. The button profile driver 114 may be configured to deploy the buttons when the cover 104 is in an open state, and stow the buttons when the cover 104 is in a closed state. Or the button profile driver 114 may be configured to stow the buttons until the user presses a button, touches a touch sensor, moves the device, and so forth.

In some implementations the button profile driver 114 may be configured to provide additional functions. For example, haptic output may be produced by changing current/voltage waveforms which provide pre-determined physical sensations to user. In another implementation, the button profile driver 114 may modulate the solid-state actuator within the variable profile button 112 at audio frequencies to generate audible output.

A button press detector 116 is configured to detect touches to the buttons based at least in part upon changes in one or more characteristics of the button. For example, the button press detector 116 may be configured to scan for changes in capacitance, resistance, impedance, or a combination thereof to determine when the button has been displaced.

A side view 118 illustrates a cross-section of the device along line C1. In this illustration a stowed variable profile button 120 at in the first position is shown as is a deployed variable profile button 122 in the second position. A deployed height "H" is shown, illustrating an elevation difference between the stowed and deployed positions. As shown here, in some implementations the stowed height may correspond to a surface of the device, such that when stowed a relatively planar surface is presented to the user.

An electroactive polymer 124 is shown here as the solid-state actuator. As described above, the solid-state actuator is configured to transition between two or more shapes upon application of electric, magnetic, chemical, or other external input. For example, upon application of a voltage exceeding about two hundred volts, an electroactive polymer will contract along a line extending from one electrode to another. Other solid-state actuators include, but are not limited to, dielectric electroactive polymers, ionic polymer-metal composites, piezoelectric ceramics, and so forth.

Figure 2:
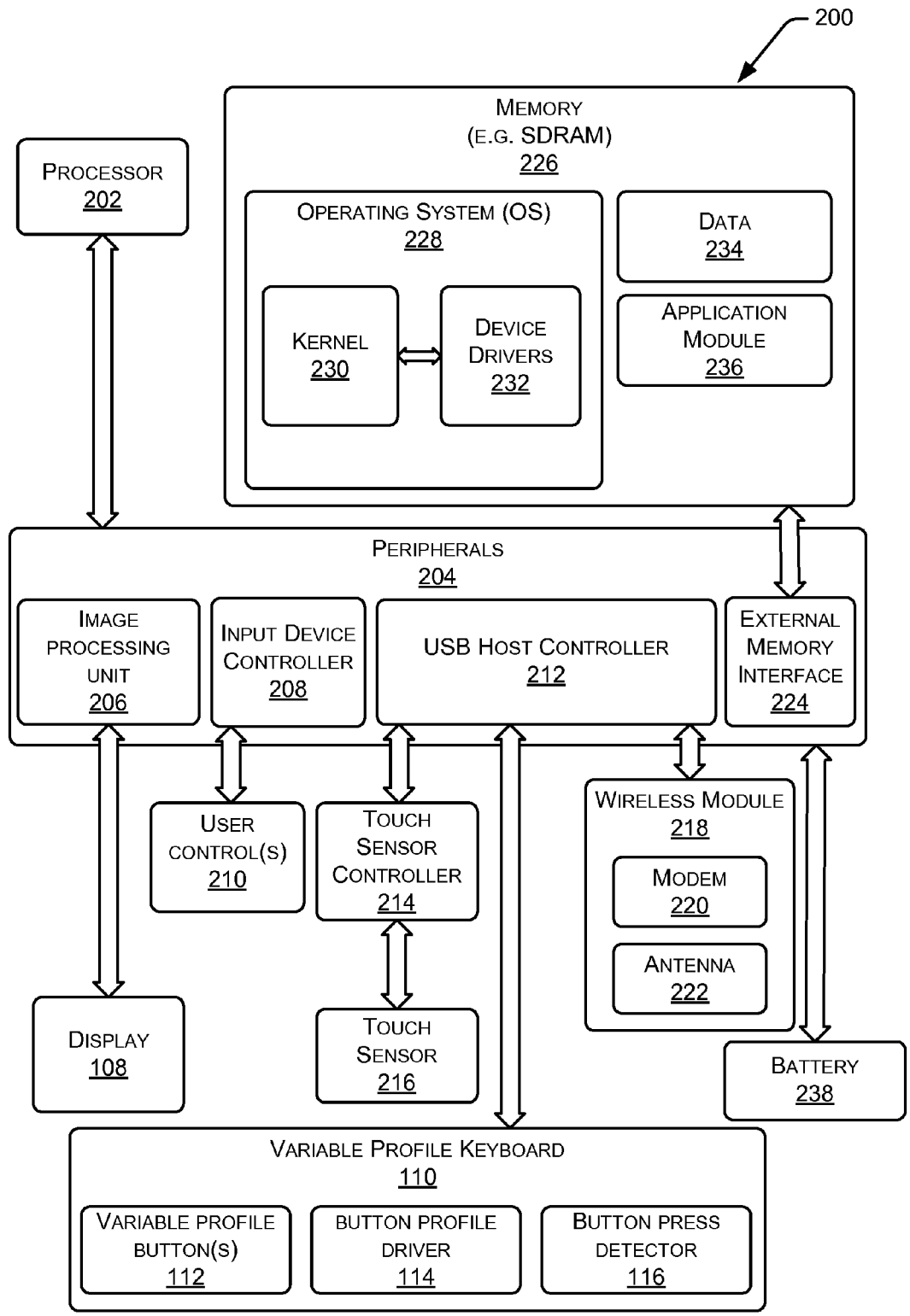
FIG. 2 is an illustrative schematic of the electronic device with the variable profile keyboard and associated drivers and detectors.

FIG. 2 is an illustrative schematic 200 of the electronic device 100 of FIG. 1. In a very basic configuration, the device 100 includes components such as a processor 202 and one or more peripherals 204 coupled to the processor 202. Each processor 202 may itself comprise one or more processors.

An image processing unit 206 is shown coupled to one or more display components 108 (or "displays"). In some implementations, multiple displays may be present and coupled to the image processing unit 206. These multiple displays may be located in the same or different enclosures or panels. Furthermore, one or more image processing units 206 may couple to the multiple displays.

The display 108 may present content in a human-readable format to a user. The display 108 may be reflective, emissive, or a combination of both. Reflective displays utilize incident light and include electrophoretic displays, interferometric modulator displays, cholesteric displays, and so forth. Emissive displays do not rely on incident light and, instead, emit light. Emissive displays include backlit liquid crystal displays, time multiplexed optical shutter displays, light emitting diode displays, and so forth. When multiple displays are present, these displays may be of the same or different types. For example, one display may be an electrophoretic display while another may be a liquid crystal display. The display 108 may be color or monochrome.

For convenience only, the display 108 is shown in FIG. 1 in a generally rectangular configuration. However, it is understood that the display 108 may be implemented in any shape, and may have any ratio of height to width. Also, for stylistic or design purposes, the display 104 may be curved or otherwise non-linearly shaped. Furthermore the display 108 may be flexible and configured to fold or roll.

The content presented on the display 108 may include electronic books or "eBooks." For example, the display 108 may depict the text of the eBooks and also any illustrations, tables, or graphic elements that might be contained in the eBooks. The terms "book" and/or "eBook", as used herein, include electronic or digital representations of printed works, as well as digital content that may include text, multimedia, hypertext, and/or hypermedia. Examples of printed and/or digital works include, but are not limited to, books, magazines, newspapers, periodicals, journals, reference materials, telephone books, textbooks, anthologies, instruction manuals, proceedings of meetings, forms, directories, maps, web pages, and so forth. Accordingly, the terms "book" and/or "eBook" may include any readable or viewable content that is in electronic or digital form.

The device 100 may have an input device controller 208 configured to accept input from a keypad, keyboard, or other user actuable controls 210. These user actuable controls 210 may have dedicated or assignable operations. For instance, the actuable controls may include page turning buttons, a navigational keys, a power on/off button, selection keys, joystick, touchpad, and so on.

The device 100 may also include a USB host controller 212. The USB host controller 212 manages communications between devices attached to a universal serial bus ("USB") and the processor 202 and other peripherals.

FIG. 2 further illustrates that the device 100 includes a touch sensor controller 214. The touch sensor controller 214 couples to the processor 202 via the USB host controller 212 (as shown). In other implementations, the touch sensor controller 214 may couple to the processor via the input device controller 208, inter-integrated circuit ("I²C"), universal asynchronous receiver/transmitter ("UART"), or serial peripheral interface bus ("SPI"), or other interfaces. The touch sensor controller 214 couples to a touch sensor 216. In some implementations multiple touch sensors 216 may be present.

The touch sensor 216 may comprise various technologies including interpolating force-sensing resistance (IFSR) sensors, capacitive, magnetic, force sensitive resistors, acoustic, optical, and so forth. The touch sensor 216 may be configured such that user input through contact or gesturing relative to the device 100 may be received.

The variable profile keyboard 110 is shown coupled to the USB host controller 212. In other implementations the variable profile keyboard 110 may be coupled via other interfaces such as the input device controller 208. The variable profile keyboard 110 includes the variable profile buttons 112, button profile driver 114, and the button press detector 116. In some implementations the button profile driver 114, button press detector 116 may be incorporated into a same assembly as the variable profile buttons 112, or may be separate and coupled, such as via a ribbon cable, flexible printed circuit, and so forth.

The USB host controller 212 may also couple to a wireless module 218 via the universal serial bus. The wireless module 218 may allow for connection to wireless local or wireless wide area networks ("WWAN"). Wireless module 218 may include a modem 220 configured to send and receive data wirelessly and one or more antennas 222 suitable for propagating a wireless signal. In other implementations, the device 100 may include a wired network interface.

The device 100 may also include an external memory interface ("EMI") 224 coupled to external memory 226. The EMI 224 manages access to data stored in external memory 226. The external memory 226 may comprise Static Random Access Memory ("SRAM"), Pseudostatic Random Access Memory ("PSRAM"), Synchronous Dynamic Random Access Memory ("SDRAM"), Double Data Rate SDRAM ("DDR"), Phase-Change RAM ("PCRAM"), or other computer-readable storage media.

The external memory 226 may store an operating system 228 comprising a kernel 230 operatively coupled to one or more device drivers 232. The device drivers 232 are also operatively coupled to peripherals 204, such as the variable profile keyboard 110. The external memory 226 may also store data 234, which may comprise content objects for consumption on the device 100, executable programs, databases, user settings, configuration files, device status, and so forth.

Executable instructions comprising an application module 236 may also be stored in the memory 226. The application module 236 may be configured to receive data from the variable profile keyboard 110, initiate changes in button positions, and so forth.

One or more batteries 238 provide operational electrical power to components of the device 100 for operation when the device is disconnected from an external power supply. The device 100 may also include one or more non-illustrated peripherals, such as a hard drive using magnetic, optical, or solid-state storage to store information, a firewire bus, a Bluetooth™ wireless network interface, camera, global positioning system, orientation sensor, accelerometer, magnetometer, PC Card component, and so forth.

Couplings, such as that between the variable profile keyboard 110 and the USB host controller 212, are shown for emphasis. There are couplings between many of the components illustrated in FIG. 2, but graphical arrows are omitted for clarity of illustration.

Illustrative Variable Profile Button

Figure 3:
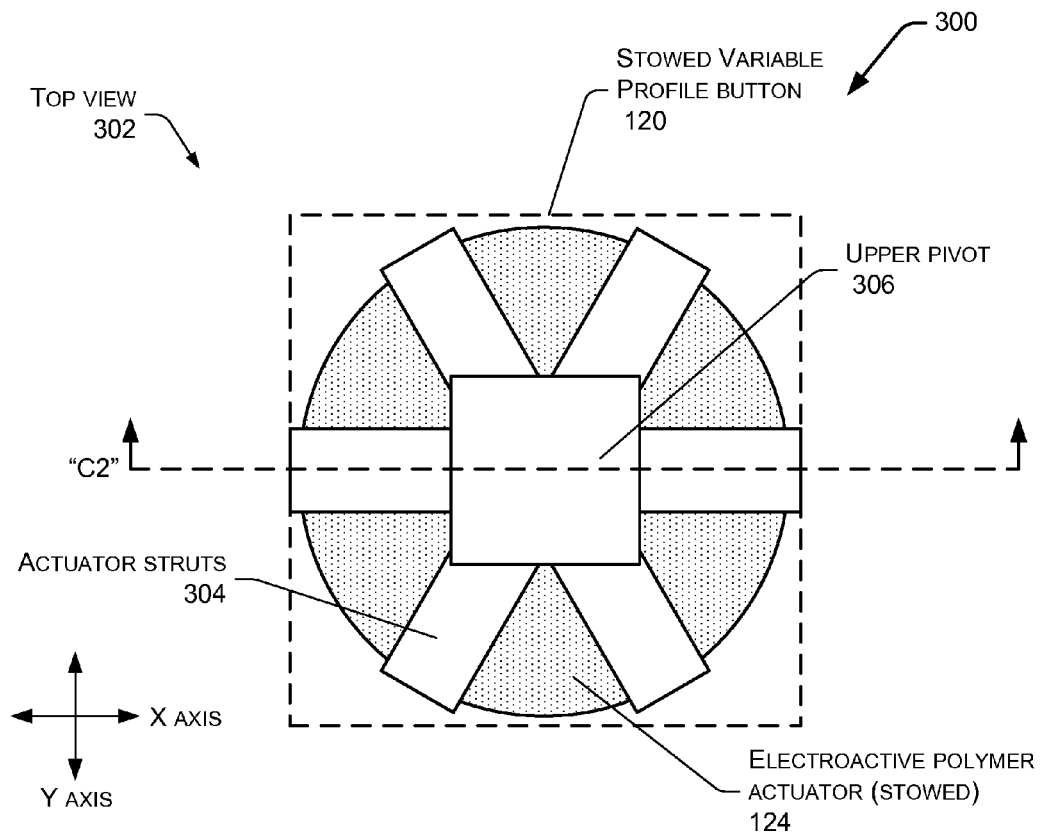
FIG. 3 illustrates a variable profile button in a stowed configuration.
Figure 3:
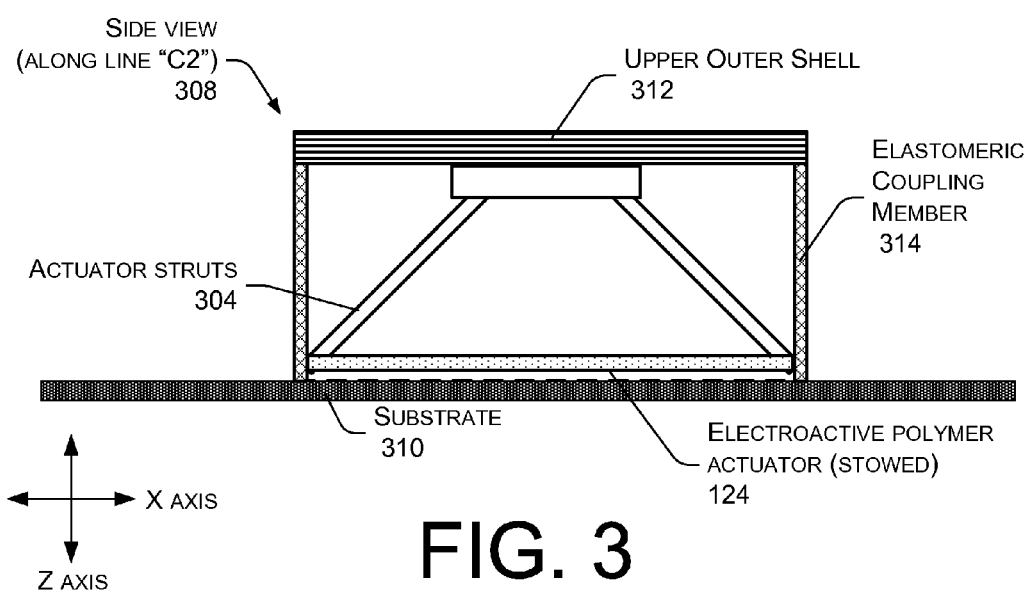

FIG. 3 illustrates a variable profile button in a stowed configuration 300. A top view 302 shows a variable profile button 112 which may have one or more actuator struts 304. In some implementations more or fewer actuator struts 304 may be used. These struts may have various shapes including rectangles, strips, triangles, and so forth. The actuator struts couple to an upper pivot 306 as well as the electroactive polymer actuator 124 or other solid-state actuator. As shown here, the electroactive polymer actuator 124 is configured into a flat disk or ellipsoidal shape. In other implementations other configurations may be used, such as discrete strips, strands, squares, triangles, and so forth.

A side view 308 along line C2 shows the actuator struts 304 which may be coupled to a substrate 310. The substrate 310 may comprise a printed circuit board, backplane, polymer, ceramic, metal, and so forth. The substrate 310 may be rigid, semi-flexible, or flexible. For example, a semi-flexible or flexible substrate may be used for a portable keyboard configured to be rolled up.

An upper outer shell 312 is coupled to the upper pivot 306. In some implementations, the upper outer shell 312 may incorporate the upper pivot 306 as well as at least a portion of the actuator struts 304. The upper outer shell 312 is configured to accept force from a touch input, such as from a user's finger. The upper outer shell 312 may also be configured with visual or tactile indicia indicative of the button's function, such as printed letters, particular textures, and so forth.

The upper outer shell 312 may be coupled to the substrate 310 via one or more elastomeric coupling members 314. These elastomeric coupling members may be disposed around at least a portion of a perimeter of the upper outer shell 312 and extend from a lower side of the upper outer shell 312 to the substrate 310 disposed under the upper outer shell. In some implementations, such as shown here, the elastomeric coupling member 314 may be coupled to the substrate 310 such that the button is biased to remain in the stowed position when the electroactive polymer actuator 124 is in the stowed state. For example, the elastomeric coupling member 314 may be configured to pull the upper outer shell 312 back to the stowed position when no power is applied to the solid-state actuator. In other implementations, other biasing mechanisms may be used such as springs, living hinges, and so forth.

The elastomeric coupling member 314 may in some cases comprise a conductive material, and be configured to carry an electrical signal to at least a portion of the solid-state actuator. For example, the solid-state actuator may be coupled via two electrodes to the button profile driver 114. A first electrode may be disposed on the substrate 310 and in contact with at least a portion of the solid-state actuator, while a second electrode is disposed on the underside of the upper outer shell 312 and is configured to be at least partly in contact with another portion of the solid-state actuator. An electrical signal may be conveyed from a conductive trace or wire on the substrate 310 to the second electrode via the conductive elastomeric coupling member 314.

The elastomeric coupling member 314 may comprise silicon, rubber, fluoroelastomer, perfluoroelastomer, ethylene-vinyl acetate, and so forth. The elastomeric coupling member 314 may be configured to be permeable to gasses such as oxygen, nitrogen, and so forth.

Figure 4:
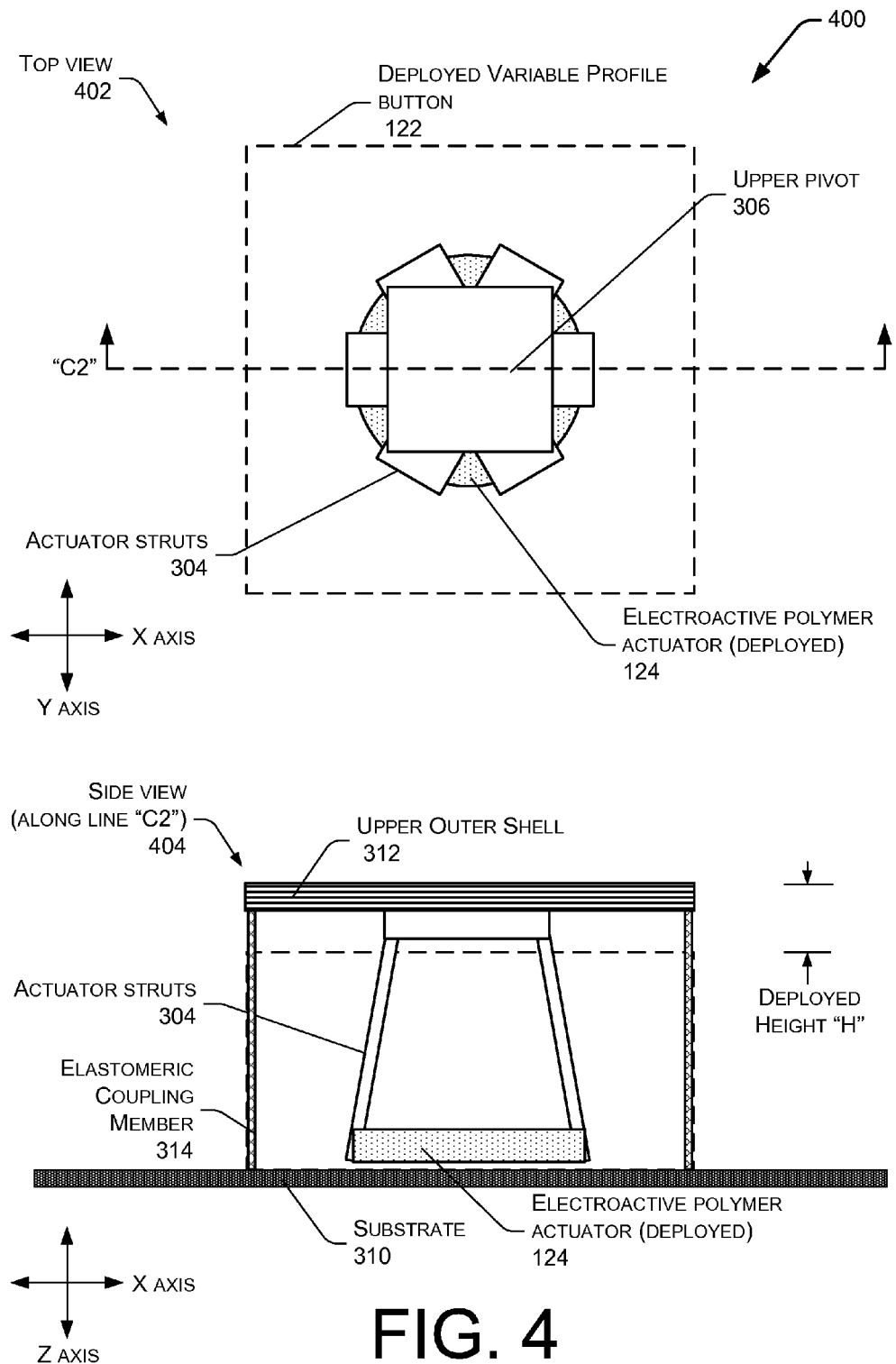
FIG. 4 illustrates the variable profile button of FIG. 3 in the deployed configuration.

FIG. 4 illustrates the variable profile button of FIG. 3 in the deployed configuration 400. In this illustration, the button profile driver 114 is providing an input to the electroactive polymer 124 which has caused the electroactive polymer 124 to change shape. A top view 402 depicts the changes in position of the actuator struts 304 relative to FIG. 3 above. This results from the change in physical shape of the electroactive polymer actuator 124 which has contracted, pulling the actuator struts 304 in towards a center of the variable profile button 112.

A side view 404 along line C2 shows the now altered profile resulting in the shape change of the electroactive polymer 124. As illustrated here, as a result of activation by the button profile driver 114, the electroactive polymer 124 is shorter along an X axis and taller along the Z axis. As a result of the deformation of the solid-state actuator, the upper outer shell 312 has been elevated relative to the substrate 310 to the deployed height "H." By varying the actuator mechanism, configuration of the solid-state actuator, and so forth, the deployed height or key travel may be increased or decreased. Furthermore, in some implementations, the button profile driver 114 may be configured to provide an intermediate deployed height, such as one-half a maximum deployed height by varying an input such as voltage applied to the electroactive polymer actuator 124.

Figure 5:
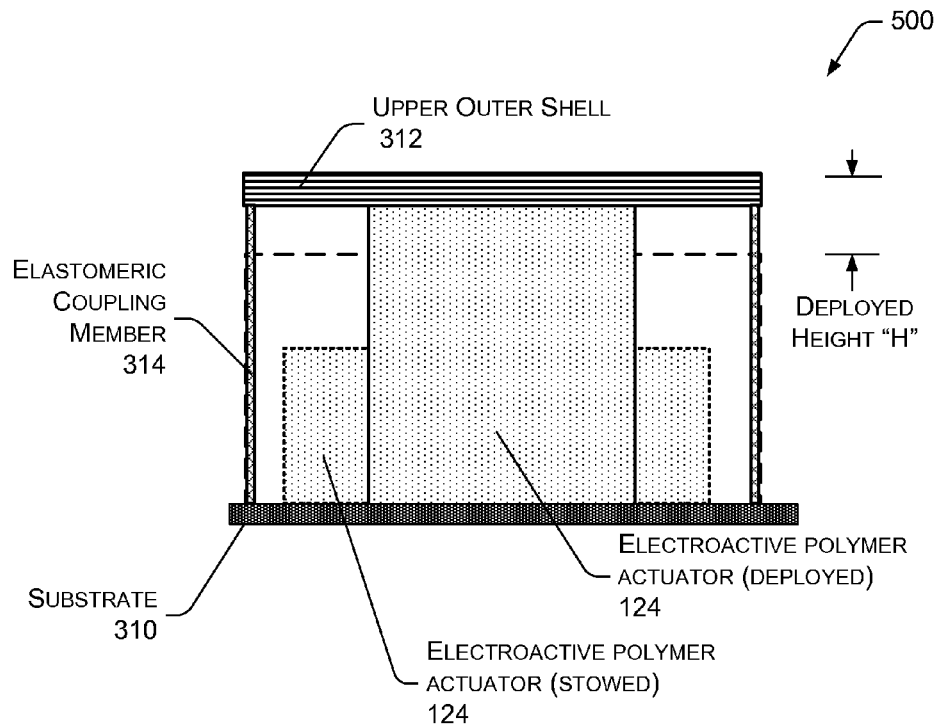
FIG. 5 illustrates an additional implementation of the variable profile button with a strutless actuator.

FIG. 5 illustrates an additional implementation of the variable profile button with a strutless actuator 500. The strutless variable profile button 500 may comprise the solid-state actuator such as the electroactive polymer 124 shown here which couples directly to the upper outer shell 312.

In this implementation, the deformation alone of the solid-state actuator results in the displacement of the upper outer shell 312 relative to the substrate. A dotted line indicates the electroactive polymer actuator 124 in the stowed position. In some situations, the action of the solid-state actuator may be reversed, allowing for both a push and a pull, depending upon input signal. For example, by reversing an applied voltage the electroactive polymer actuator 124 may affirmatively transition from the deployed position to the stowed position, in effect "pulling" the upper outer shell 312 towards the substrate 310.

As described above, the elastomeric coupling member 314 may be used to bias the upper outer shell 312 to aid in retraction of the upper outer shell 312 and resume a stowed position. The elastomeric coupling member 314 may also serve to minimize dust or other contamination of the actuator by extending around substantially all of the perimeter of the upper outer shell 312. For example, a small opening may be provided to allow ambient atmosphere to flow into and out of a volume defined by the upper outer shell 312, elastomeric coupling members 314, and the substrate 310. In some implementations, the elastomeric coupling member 314 may seal the upper outer shell 312 to the substrate 310 but remain permeable to one or more gasses. This permeability prevents "ballooning" of the button which may result in adverse performance, poor tactile response, device damage, and so forth.

Figure 6:
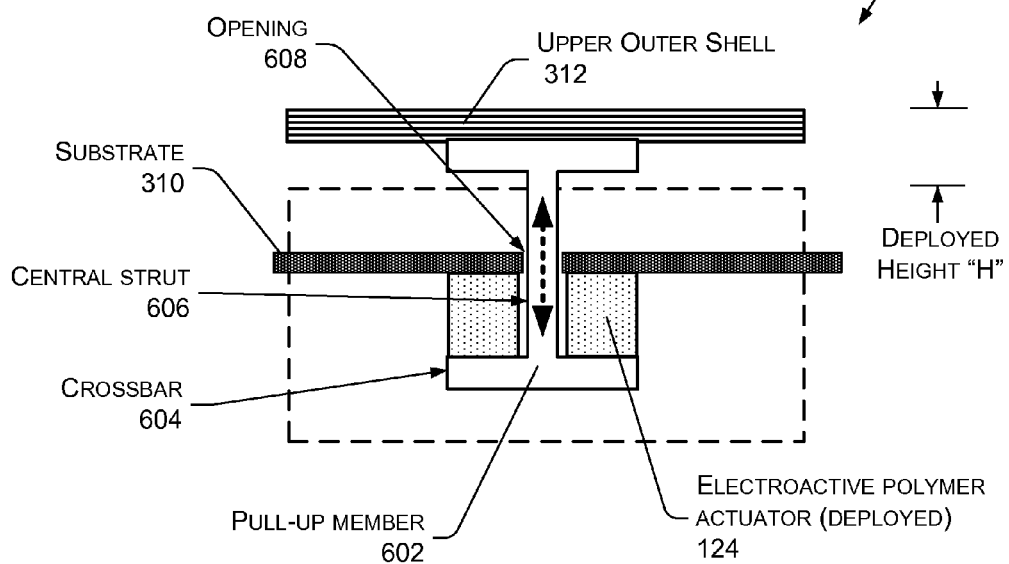
FIG. 6 illustrates an additional implementation of the variable profile button with a pull-up member.

FIG. 6 illustrates an additional implementation of the variable profile button with a pull-up member 600. In this implementation, a pull-up member 602 comprising a crossbar 604 and a central strut 606 is disposed such that at least a portion of the central strut 606 extends from an underside of the substrate 310 through an opening 608 in the substrate 310 to a front side of the substrate and couples mechanically to the upper outer shell 312. The pull-up member 602 may comprise other arrangements, for example having cross sections of an inverted "T", "C", and so forth. In some implementations, the upper outer shell 312 and the pull-up member 602 may be a single structure. The portion of the pull-up member underneath the substrate pull-up member is coupled via the solid-state actuator to the underside of the substrate 310. When in the deployed state shown here, the solid-state actuator such as the electroactive polymer 124 contracts, pulling the crossbar 604 of the pull-up member 602 towards the substrate 310. Force is transferred along the central strut 606 of the pull-up-member 604 to the upper outer shell 312, which moves to the deployed position at height "H". In another implementation, a second solid-state actuator may be disposed such that the pull-up member 602 may actively retract the upper outer shell 312 into the stowed position.

Illustrative Processes

The processes in this disclosure may be implemented by the devices described in this disclosure, or by other devices. These processes described in this disclosure are illustrated as a collection of blocks in a logical flow graph, which represent a sequence of operations that can be implemented in hardware, software, or a combination thereof. In the context of software, the blocks represent computer-executable instructions that may be stored on one or more computer-readable storage media and that, when executed by one or more processors, perform the recited operations. Generally, computer-executable instructions include routines, programs, objects, components, data structures, and the like that perform particular functions or implement particular abstract data types. The order in which the operations are described is not intended to be construed as a limitation, and any number of the described blocks can be combined in any order or in parallel to implement the processes.

Figure 7:
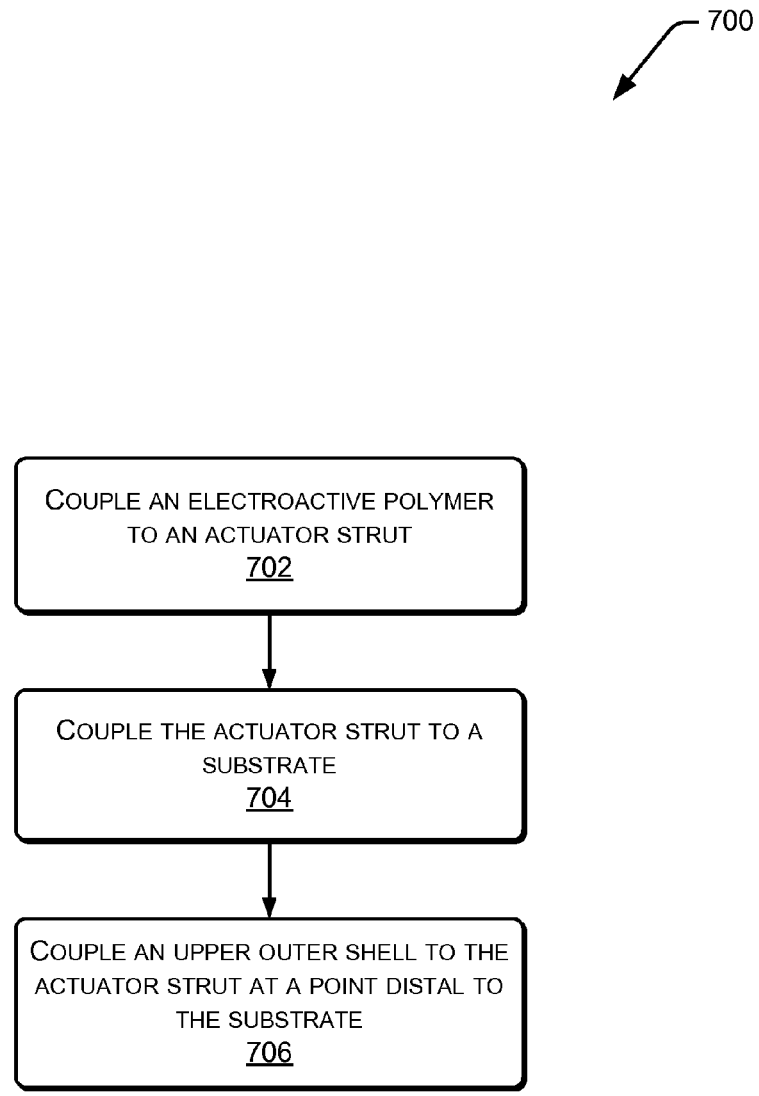
FIG. 7 is an illustrative process of assembling a variable profile button.

FIG. 7 is an illustrative process 700 of assembling the variable profile button 112. The following process is provided as one example of many possible implementations. At 702, at least a portion of the electroactive polymer 124 is coupled to an actuator strut 304 or other actuator structure. The coupling may comprise welding, soldering, bonding, adhesive, crimping, physical fastener, interference fit, and so forth.

At 704, the actuator strut 304 is coupled to the substrate 310. As above, this coupling may comprise welding, soldering, bonding, adhesive, crimping, physical fastener, interference fit, and so forth. For example, a portion of the actuator strut 304 may snap into a receptacle on or within the substrate 310.

At 706, the upper outer shell 312 is coupled to at least a portion of the actuator strut 304. The coupling may be as described above. In some implementations, the upper outer shell 312 may incorporate the actuator strut 304 as an integral member. For example, the upper outer shell 312 may have a portion which incorporates a living hinge and forms the actuator strut 304 or other actuator structure.

The process described may be accomplished via manual assembly techniques, with automated assembly equipment, or a combination thereof. The various components of the variable profile button 112 may be discrete components, sub-assemblies, integral, or contiguous extensions of one another.

Figure 8:
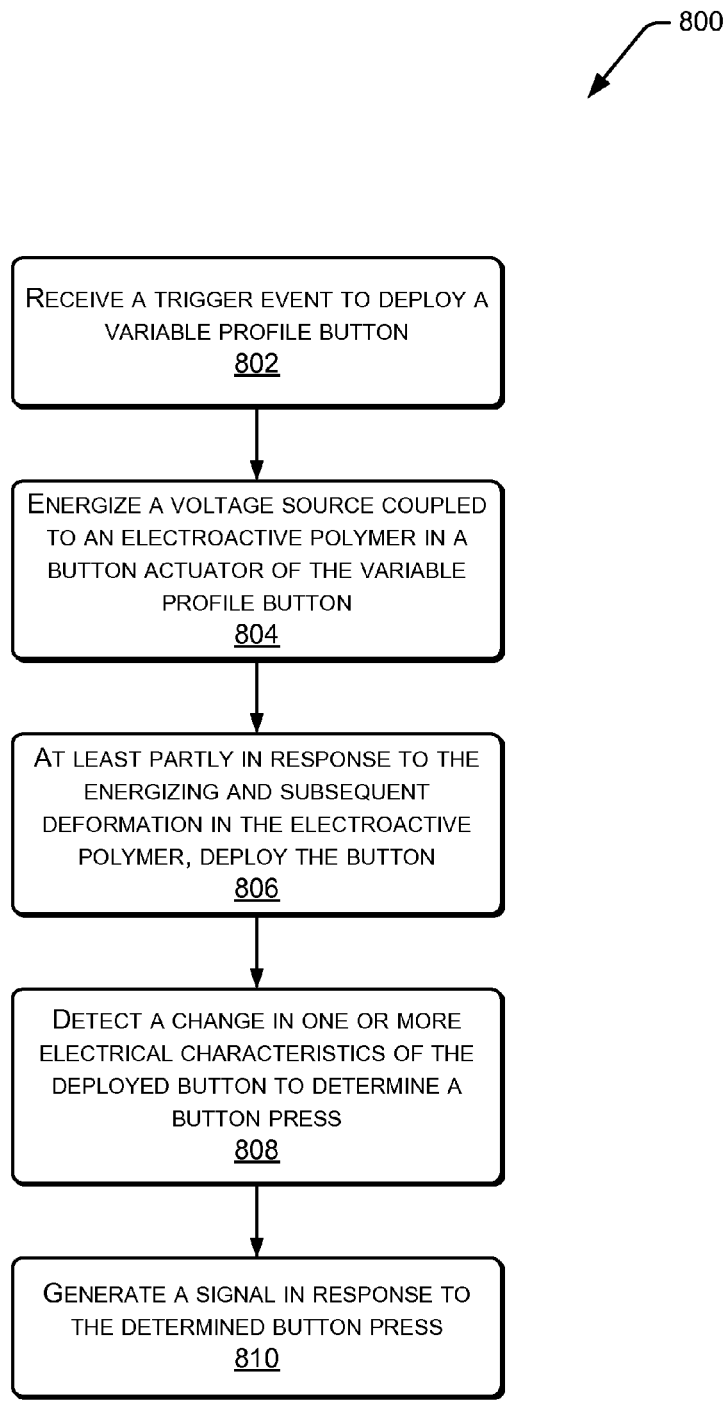
FIG. 8 is an illustrative process of deploying a variable profile button.

FIG. 8 is an illustrative process 800 of deploying the variable profile button 112. At 802, a trigger event is received to deploy one or more variable profile buttons 112. A controller such as the button profile driver 114 may receive the event. The trigger event may comprise an electronic, optical, mechanical, or other signal which is detectable by the controller.

At 804, a voltage source coupled to the electroactive polymer 124 in a button actuator of the variable profile button is energized. The voltage source may comprise voltage boost circuitry coupled to a battery or power supply and also coupled to at least a portion of the electroactive polymer 124. The voltage source is configured to generate voltages, currents, and waveforms suitable for activating the electroactive polymer 124 or another solid-state actuator. The button actuator may comprise one or more mechanical or magnetic linkages configured to transform motion resulting from deformation of the solid-state actuator into displacement of the upper outer shell 312.

At 806, at least partly in response to the energizing and subsequent deformation of the electroactive polymer 124, the variable profile button 122 transitions to a deployed state. As mentioned above, the deployed state may be configured to increase the key travel of the button upon actuation.

At 808, a change in one or more electrical characteristics are detected in the deployed button to determine a button press. For example, where the solid-state actuator comprises dielectric electroactive polymer, a change in the capacitance of the dielectric electroactive polymer may be measured. Pressing on the button causes a change in the shape of the dielectric electroactive polymer. As a result of this change in shape, the capacitance of the polymer changes. When the capacitance as detected exceeds a threshold amount, a button press may be deemed to occur. The threshold may be statically set, or dynamically varied. This detection may be performed at least in part by the button press detector 116. In other implementations, one or more other electrical characteristics may be detected including, but not limited to, capacitance, resistance, and inductance.

At 810, a signal is generated in response to the determined button press. For example, the button press detector 116 may determine that the capacitance has exceeded the threshold value and thus a button press is deemed to have occurred. The detector 116 may then generate a data signal indicating the button which was pressed.

CONCLUSION

Although the subject matter has been described in language specific to structural features and/or methodological acts, it is to be understood that the subject matter defined in the appended claims is not necessarily limited to the specific features or acts described. Rather, the specific features and acts are disclosed as illustrative forms of implementing the claims. For example, the methodological acts need not be performed in the order or combinations described herein, and may be performed in any combination of one or more acts.

What is claimed is:
1. A device comprising:
   a button profile driver configured to couple to a power source and generate a voltage sufficient to initiate a change in shape of an electroactive polymer from a first state to a second state;
   a variable profile button comprising:

the electroactive polymer wherein, when the electroactive polymer changes shape from the first shape to the second shape, at least a portion of the variable profile button is displaced from a first distance relative to a substrate to a second distance, and wherein the second distance is greater than the first distance;

one or more actuator struts coupled to the electroactive polymer and the substrate; and one or more elastomeric coupling members coupled to the substrate; and a button press detector coupled to the variable profile button and configured to detect a change in one or more electrical characteristics to determine a button press.

2. The device of claim 1, wherein the one or more actuator struts support the portion of the variable profile button relative to the substrate.

3. The device of claim 1, wherein the variable profile button comprises:

one or more pull-up members comprising a crossbar and a central strut, wherein the crossbar is coupled to an underside of the substrate with the electroactive polymer, the central strut passes through an opening in the substrate and is coupled to an upper outer shell, and wherein the underside is opposite a side presented to a user during operation.

4. The device of claim 1, wherein the electroactive polymer comprises a disc or ellipsoidal shape.

5. The device of claim 1, wherein the electroactive polymer comprises a dielectric electroactive polymer and the voltage as applied to the dielectric electroactive polymer to initiate the change in shape exceeds two hundred volts.

6. The device of claim 1, wherein the one or more electrical characteristics comprise one or more of capacitance, resistance, impedance, or a combination thereof.

7. The device of claim 1, wherein the change detected in the one or more electrical characteristics comprises a change to a capacitance, resistance, impedance, or a combination thereof of the electroactive polymer.

8. The device of claim 1, wherein:

the portion of the variable profile button that is displaced includes an upper outer shell coupled to the electroactive polymer; and the variable profile button further comprises the one or more elastomeric coupling members disposed around at least a portion of a perimeter of the upper outer shell and extending from the upper outer shell to the substrate disposed under the upper outer shell.

9. The device of claim 1, wherein the button profile driver is configured to vary the voltage to produce a haptic effect.

10. A variable profile button comprising:

an upper outer shell configured to accept an input force; and a solid-state actuator coupled to a substrate and the upper outer shell with a mechanical linkage, the solid-state actuator configured to, when active, displace the upper outer shell from a first position to a second position, relative to the substrate.

11. The variable profile button of claim 10, wherein the mechanical linkage includes one or more elastomeric coupling members coupling the upper outer shell to the substrate.

12. The variable profile button of claim 11, wherein the one or more elastomeric coupling members are disposed around at least a portion of a perimeter of the upper outer shell.

13. The variable profile button of claim 10, wherein the solid-state actuator comprises a dielectric electroactive polymer.

14. The variable profile button of claim 10, wherein the solid-state actuator comprises an ionic polymer-metal composite.

15. The variable profile button of claim 10, wherein the solid-state actuator comprises a piezoelectric ceramic.

16. The variable profile button of claim 10, wherein the solid-state actuator comprises one or more actuator struts configured to generate a displacement of the upper outer shell upon contraction or expansion of the solid-state actuator.

17. The variable profile button of claim 10, wherein the second position is a greater distance to the substrate than the first position.

18. The variable profile button of claim 10, further comprising a button press detector configured to detect a change in one or more electrical characteristics of the solid-state actuator upon application of the input force to determine a button press.

19. The variable profile button of claim 10, further comprising a button profile driver configured to provide power sufficient to activate the solid-state actuator.

20. A method comprising:

receiving a trigger event to deploy a variable profile button comprising an electroactive polymer;

energizing a voltage source coupled to the electroactive polymer in a button actuator, wherein at least partly in response to the energizing, the electroactive polymer is deformed to cause movement of a mechanical linkage for deploying the button;

detecting a change in one or more electrical characteristics of the deployed button to determine a button press; and generating a signal in response to the determined button press.

21. The method of claim 20, wherein the detecting the change comprises, at least in part, registering a change in capacitance of the electroactive polymer.

22. The method of claim 21, wherein the change in the capacitance of the electroactive polymer results from a deformation of the electroactive polymer caused by the button press.

* * * * *